(12) United States Patent
Black

(10) Patent No.: US 7,312,365 B2
(45) Date of Patent: Dec. 25, 2007

(54) PROCESS FOR LOW TEMPERATURE CLEAVAGE OF AN OXIDATION MIXTURE COMPRISING HYDROPEROXIDES

(75) Inventor: Jesse Raymond Black, Katy, TX (US)

(73) Assignee: Shell Oil Company, Houston, TX (US)

(*) Notice: Subject to any disclaimer, the term of this patent is extended or adjusted under 35 U.S.C. 154(b) by 413 days.

(21) Appl. No.: 10/761,675

(22) Filed: Jan. 21, 2004

(65) Prior Publication Data

US 2004/0162446 A1    Aug. 19, 2004

Related U.S. Application Data

(60) Provisional application No. 60/447,845, filed on Feb. 14, 2003.

(51) Int. Cl.
*C07C 37/08* (2006.01)

(52) U.S. Cl. .................................. 568/798

(58) Field of Classification Search ............... 568/798
See application file for complete search history.

(56) References Cited

U.S. PATENT DOCUMENTS

| | | | | |
|---|---|---|---|---|
| 2,632,026 A | 3/1953 | Conner, Jr. | ............ | 260/610 |
| 2,632,773 A | 3/1953 | Armstrong et al. | ......... | 260/610 |
| 2,757,209 A | 7/1956 | Joris | ............ | 260/621 |
| 3,187,055 A | 6/1965 | Armstrong et al. | ......... | 260/610 |
| 3,523,977 A | 8/1970 | Reni et al. | ............ | 260/610 |
| 3,907,901 A | 9/1975 | Feder et al. | ............ | 260/610 B |
| 4,016,213 A | 4/1977 | Yeh et al. | ............ | 260/621 C |
| 4,358,618 A | 11/1982 | Sifniades et al. | ............ | 568/385 |
| 4,431,849 A | 2/1984 | Colvin | ............ | 568/799 |
| 5,254,751 A * | 10/1993 | Zakoshansky | ............ | 568/798 |
| 5,298,667 A | 3/1994 | Iwanaga et al. | ............ | 568/385 |
| 5,304,684 A | 4/1994 | Nishida et al. | ............ | 568/385 |
| 5,530,166 A | 6/1996 | Zakoshansky et al. | ...... | 568/798 |
| 5,767,322 A | 6/1998 | Zakoshansky et al. | ...... | 568/571 |
| 5,908,962 A | 6/1999 | Zakoshansky et al. | ...... | 568/571 |
| 5,959,155 A | 9/1999 | Ohmae et al. | ............ | 568/576 |
| 6,077,977 A | 6/2000 | Gopinathan et al. | ........ | 568/571 |
| 6,465,695 B1 | 10/2002 | Fulmer et al. | ............ | 568/571 |
| 6,486,365 B1 | 11/2002 | Fulmer et al. | ............ | 568/768 |

FOREIGN PATENT DOCUMENTS

| | | |
|---|---|---|
| DE | 1443329 | 1/1970 |
| DE | 2300903 | 1/1972 |
| EP | 0399776 | 5/1990 |
| EP | 0548986 A1 | 6/1993 |
| EP | 0548986 A1 | 6/1993 |
| EP | 0578194 B1 | 1/1994 |
| EP | 0578194 B1 | 1/1994 |
| EP | 1088807 A1 | 4/2001 |
| EP | 1088807 A1 | 4/2001 |

(Continued)

OTHER PUBLICATIONS

International Search Report of Jul. 23, 2004.

*Primary Examiner*—Yvonne Eyler
*Assistant Examiner*—Kellette Gale

(57) ABSTRACT

A process for cleaving an oxidation product comprising s-butyl benzene hydroperoxide and/or cumene hydroperoxide which reduces the production of non-recoverable by-products from dimethylbenzyl alcohol (DMBA) and ethyl methyl benzyl carbinol (EMBA).

142 Claims, 1 Drawing Sheet

FOREIGN PATENT DOCUMENTS

| | | |
|---|---|---|
| EP | 01088809 A1 | 4/2001 |
| EP | 1088809 A1 | 4/2001 |
| JP | 62-114922 | 5/1987 |
| JP | 03287574 | 12/1991 |
| JP | 2001097901 A * | 4/2001 |
| WO | 00/14042 | 3/2000 |

* cited by examiner

PROCESS FOR LOW TEMPERATURE CLEAVAGE OF AN OXIDATION MIXTURE COMPRISING HYDROPEROXIDES

The present application claims the benefit of U.S. Provisional Patent Application Ser. No. 60/447,845, filed Feb. 14, 2003.

FIELD OF THE APPLICATION

The present application relates to a process for cleaving an oxidation product comprising s-butyl benzene hydroperoxide and/or cumene hydroperoxide which reduces the production of non-recoverable by-products from dimethylbenzyl alcohol (DMBA) and ethyl methyl benzyl carbinol (EMBA).

BACKGROUND

In general, phenol is manufactured by oxidizing cumene to form the hydroperoxide of cumene, followed by cleavage of the cumene hydroperoxide with an inorganic acid such as sulfuric acid to form a cumene hydroperoxide cleavage product. Some processes oxidize s-butylbenzene, either alone or in combination with cumene, to produce s-butylbenzene hydroperoxide.

A cumene oxidation product generally contains dimethylbenzyl alcohol (DMBA). Where the oxidation feed comprises s-butylbenzene, the oxidation product also generally comprises ethyl methyl benzyl carbinol (EMBA). It is desirable to maximize conversion of DMBA in the oxidation product to α-methyl styrene (AMS), and to maximize conversion of EMBA in the oxidation product to α-methyl styrene (AES) and 2-phenyl-2-butene (2P2B) because these compounds can be hydrogenated to produce cumene and s-butylbenzene for recycle back to the oxidation reactors, which increases overall conversion efficiency.

Unfortunately, many cleavage reactions are run at relatively high reaction temperatures. For example, the reaction temperature in typical boiling pot reactions is from about 75° C. to about 85° C. At such high reaction temperatures, significant amounts of DMBA, EMBA, product AMS, product AES, and product 2P2B are converted to "non-recoverable by-products."

Methods are needed which decrease the loss of DMBA and EMBA to non-recoverable by-products.

SUMMARY

The present application provides a process for cleaving one or more hydroperoxides selected from the group consisting of s-butylbenzene hydroperoxide, cumene hydroperoxide, and combinations thereof. The process comprises:
feeding a cleavage reaction feed to a cleavage reactor to produce a cleavage reaction mixture comprising the one or more hydroperoxides; and
subjecting the cleavage reaction mixture to cleavage reaction conditions effective to produce a cleavage reaction product comprising phenol and one or more component selected from the group consisting of methyl ethyl ketone (MEK), acetone, and combinations thereof;
wherein the cleavage reaction conditions comprise a cleavage reaction temperature which is sufficiently high to cleave a majority of the one or more hydroperoxides but sufficiently low to produce a first quantity of non-recoverable byproducts from components selected from the group consisting of dimethylbenzyl alcohol (DMBA), ethyl methyl benzyl carbinol (EMBA), and combinations thereof, the first quantity of said non-recoverable by-products being less than a second quantity of said non-recoverable byproducts produced from said components by the same process at a cleavage reaction temperature of 75° C. or higher.

DETAILED DESCRIPTION

Figure 1:
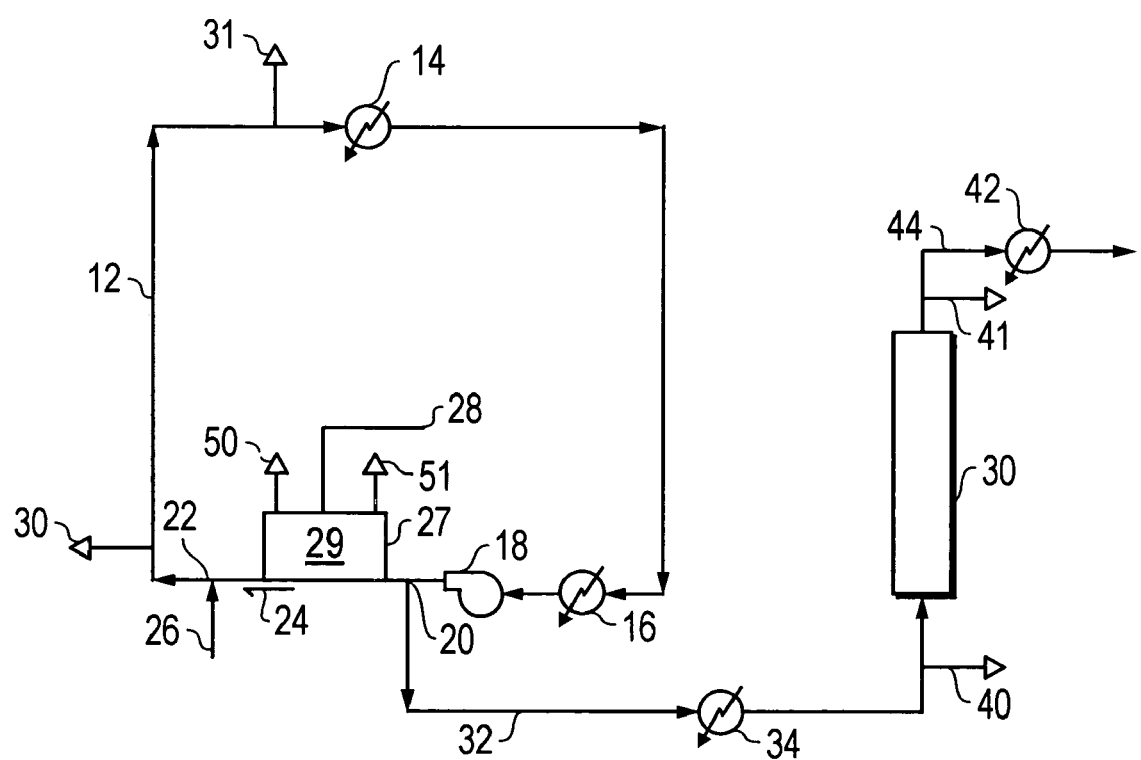
FIG. 1 is a schematic diagram of a preferred embodiment of the cleavage process.

The "low temperature cleavage" of the present application is run at cleavage temperatures which decrease the loss of DMBA and EMBA to non-recoverable by-products.

Low temperature cleavage will be described with reference to a preferred embodiment in which the cleavage zone comprises a first cleavage reactor and a second cleavage reactor. However, low temperature cleavage encompasses the use of one or more reactors, and is not limited to a system using two reactors.

The cleavage reaction feed comprises from about 0.5 wt. % to about 2 wt. % water, a ketone stream selected from the group consisting of an acetone stream, a MEK stream, or a mixed acetone/MEK stream, and hydroperoxides selected from the group consisting of s-butylbenzene hydroperoxide, cumene hydroperoxide, and combinations thereof. It has been found that a ketone feed, preferably from the ketone recovery zone(s) is an aid in reducing production of non-recoverable by-products from DMBA and/or EMBA. When the cleavage reaction occurs in a single reactor, the cleavage reaction mixture is first exposed to first reaction conditions (described below) comprising a relatively low temperature, and subsequently exposed to second reaction conditions (also described below) in the same reactor. In a preferred embodiment, the initial cleavage reaction feed is a first cleavage reactor feed 26 (FIG. 1) to a first cleavage reactor 12.

The cleavage reactor(s) may be a variety of reactor types. Preferred reactors include, but are not necessarily limited to plug-flow reactors ("PFR's"); plug-flow reactors with recycle (PFRR's); and continuous stirred tank reactors (CSTR's).

The first cleavage reactor 12 can be a stirred tank reactor with associated internal or external heat exchange equipment effective to maintain the first cleavage reaction mixture at the first cleavage reaction temperature. In a preferred embodiment the first cleavage reactor 12 is a pipeline loop reactor comprising one or more heat exchangers 14, 16 at appropriate locations to provide cooling sufficient to maintain the first cleavage reaction mixture at the first cleavage reaction temperature. Generally, the first cleavage reaction temperature is from about 45° C. to about 70° C. In a preferred embodiment, the first cleavage reaction temperature is from about 45° C. to about 60° C., more preferably from about 45° C. to about 55° C. The first cleavage reaction pressure is maintained sufficiently high to maintain the first cleavage reaction mixture in the liquid phase. Operating at 0.5 atmosphere or more generally is sufficient to maintain the first cleavage reaction mixture in the liquid phase.

A pump 18 is installed in the pipeline loop to provide for recirculation of a recycle flow of the first cleavage reaction mixture through the first cleavage reactor 12. A second portion of the first cleavage reaction mixture, the "first cleavage reaction product," is withdrawn from the pipeline loop reactor at a withdrawal point 20 located a short distance upstream of the feed point 22 for the first cleavage reactor feed 26. The recycle flow 24 through the pipeline loop of the first cleavage reactor 12 is much larger than the flow of the first cleavage reactor feed 26 (sometimes referred to as the "first cleavage reactor feed flow 26"). Preferably, the ratio of the recycle flow 24 to the first cleavage reactor feed flow 26 is from about 10:1 to about 100:1 on a weight basis, and more preferably from about 20:1 to 40:1 on a weight basis.

The first cleavage reaction conditions comprise a first cleavage reaction residence time effective to cleave from about 95% to about 98% of hydroperoxides selected from the group consisting of s-butylbenzene hydroperoxide, cumene hydroperoxide, and combinations thereof. Depending upon the hydroperoxides present in the first cleavage reaction mixture, the hydroperoxides are converted to phenol and a compound selected from the group consisting of methyl ethyl ketone (MEK), acetone, and combinations thereof. Generally, the first cleavage reaction residence time is from about 1 minute to about 10 minutes.

The first cleavage reaction conditions comprise an acid catalyst effective to catalyze the cleavage of s-butylbenzene hydroperoxide and (if present) cumene hydroperoxide. Suitable acid catalysts include but are not necessarily limited to sulfuric acid, sulfuric acid anhydride, perchloric acid, and phosphoric acid. A preferred acid catalyst is sulfuric acid. In a preferred embodiment, the acid catalyst 28 (preferably concentrated sulfuric acid), is added to a reaction mixture side stream 27 at one or more acid addition points 29. The reaction mixture side stream is located between the first cleavage reaction product withdrawal point 20 and the first cleavage reactor feed point 22.

The acid catalyst is used in an amount of from about 0.005% to about 0.1% by weight based on the first cleavage reactor feed flow 26. Concentrated sulfuric acid and other suitable acid catalysts are commercially available from a variety of sources.

The first cleavage reaction product 32 is fed to a second cleavage reactor 30, preferably a once through plug flow reactor, to produce a second cleavage reaction mixture. The second cleavage reactor 30 is operated at second cleavage reaction conditions effective to produce a second cleavage reaction product 44 (SCRP). The first cleavage reaction product preferably is heated to a second cleavage reaction temperature and maintained in the second cleavage reactor 30 for a second cleavage reaction residence time effective to perform one or more, preferably all of the following functions: cleave greater than 95 wt. % of remaining hydroperoxides present in the first cleavage reaction product; convert 60 wt. % or more, preferably 75 wt. % or more, preferably 85 wt. % or more of DMBA (if present) in the first cleavage reaction product to AMS; and, convert 60 wt. % or more, preferably 75 wt. % or more, preferably 85 wt. % or more of EMBA (if present) in the first cleavage reaction product to AES and 2P2B. In this preferred embodiment, selectivity of conversion of DMBA to AMS and/or of EMBA to AES and 2P2B is maximized. Generally the second cleavage reaction residence time is from about 5 seconds to about 1 minute.

Suitably, the second cleavage reaction conditions comprise a second cleavage reaction temperature of from about 60° C. to about 130° C., preferably from about 70° C. to about 120° C. The second cleavage reaction conditions also comprise a second cleavage reaction pressure which, when combined with the second cleavage reaction temperature, is sufficient to maintain the second cleavage reaction mixture in the liquid phase. At the foregoing temperatures, a pressure of about 30 psig or more is sufficient. The second cleavage reaction product 44 is withdrawn from the second cleavage reactor 30 and passed to additional stages for recovering the cleavage products.

By increasing the yield of AMS, AES, and 2P2B, the low temperature initial cleavage effectively reduces the amount of cumene and s-butylbenzene required to co-produce a given amount of phenol and MEK and/or acetone. Conversion efficiency is improved and the formation of non-recoverable by-products during cleavage is reduced.

Depending on the ratio of s-butylbenzene hydroperoxide to cumene hydroperoxide, the cleavage produces a second cleavage reaction product 44 with molar acetone:phenol ratios from about 0.8:1 to about 0.23:1 Molar MEK:phenol ratios in the second cleavage reaction product 44 are from about 0.2:1 to about 0.77:1. In a most preferred embodiment, the acetone to phenol ratio in the second cleavage reaction product 44 varies from about 0.44:1 to about 0.25:1.

Reactions which occur at lower temperatures occur in the early cleavage stages, preferably in the first cleavage reaction, which occurs in the first cleavage reactor 12. About 95% to about 98% conversion of hydroperoxides to phenol and MEK and/or acetone is achieved in the first cleavage reactor 12. Reactions which require higher temperatures occur in the later cleavage stages, preferably in the second cleavage reactor 30. The conversion of DMBA to AMS and EMBA to AES and 2P2B require relatively high temperatures of from about 70° C. to about 130° C. and these reactions are postponed, preferably until the first cleavage reaction product 32 reaches the second cleavage reactor 30. At this point, little hydroperoxide remains to be cleaved. The second cleavage reaction conditions can be optimized to maximize the conversion of DMBA to AMS and EMBA to AES and 2P2B.

In a preferred embodiment, the safety of the cleavage reaction is enhanced compared to other embodiments. By using a pipeline loop reactor as the first cleavage reactor 12, it is possible to make multiple exotherm measurements to verify that the reaction is being carried properly and to control the amount of acid catalyst added to the first cleavage reaction mixture side stream 27. In typical boiling pot cleavage reactors, acid addition typically is controlled by the single exotherm measurement taken at the sulfuric acid addition point. The single exotherm measurement is made by pumping a small amount of the cleavage reactor mixture out of the reactor at the acid addition point and mixing that small amount of the cleavage reaction mixture with acid. The exotherm generated upon acid addition is measured for process control and to determine if a shutdown is required for safety purposes. If the reaction is running well, then the exotherm measured is moderate (typically 15° C.). If the reaction is running too fast, then no exotherm is measured. If the exotherm is large (about 25° C. or more), then the reaction is running too slowly. The risk of the reaction running too slowly is that a runaway reaction can occur when additional acid is added.

Plug flow reactors (PFR's) and plug flow reactors with recycle (PFRR's) are especially adaptable to multiple exotherm measurements. Controlling acid addition based on multiple exotherm measurements lowers the risk of adding too little or too much acid catalyst to the first cleavage reactor 12 due to an incorrect exotherm measurement by any one failed control system component, and essentially decouples safety components from control components.

In a preferred embodiment, the exotherm preferably is measured at multiple locations. The exotherm is measured across one or more reaction mixture exotherm measurement points, preferably a first reaction mixture side stream exotherm measurement point 51 (or a first RMSEM point 51) and a second RMSEM point 50 along the reaction mixture side stream 27. The exotherm also preferably is measured in the first cleavage reactor 12 across one or more first cleavage reactor (FCR) exotherm measurement points, preferably a first FCR exotherm measurement point 30 and a second FCR exotherm measurement point 31 along the first cleavage reactor 12. The exotherm also preferably is measured across the second cleavage reactor, preferably across a second cleavage reactor (SCR) entry exotherm measurement point 40 and a second SCR exit measurement point 41.

The second cleavage reaction product 44 generally is fed to a neutralization apparatus and may be treated using known procedures for producing phenol and other products, depending upon the oxidation feed.

Persons of ordinary skill in the art will recognize that many modifications may be made to the foregoing without departing from the spirit and scope thereof. The embodiment described herein is meant to be illustrative only and should not be taken as limiting the invention, which will be defined in the claims.

I claim:

1. A process for cleaving one or more hydroperoxides selected from the group consisting of s-butylbenzene hydroperoxide, cumene hydroperoxide, and combinations thereof, the process comprising:
   feeding a cleavage reaction feed to a cleavage reactor to produce a cleavage reaction mixture comprising the one or more hydroperoxides wherein the first cleavage reactor comprises a pipeline loop reactor comprising one or more heat exchangers effective to maintain the cleavage reaction mixture at a first cleavage reaction temperature; and
   subjecting the cleavage reaction mixture to cleavage reaction conditions effective to produce a cleavage reaction product comprising phenol and one or more components selected from the group consisting of methyl ethyl ketone (MEK), acetone, and combinations thereof;
   wherein the cleavage reaction conditions comprise a cleavage reaction temperature of less than 75° C. which is sufficiently high to cleave a majority of the one or more hydroperoxides but sufficiently low to produce a first quantity of non-recoverable byproducts from components selected from the group consisting of dimethylbenzyl alcohol (DMBA), ethyl methyl benzyl carbinol (EMBA), and combinations thereof, the first quantity of said non-recoverable byproducts being less than a second quantity of said non-recoverable byproducts produced by the same process at a cleavage reaction temperature of 75° C. or higher.

2. The process of claim 1 wherein:
   wherein said cleavage reaction feed comprises from about 0.5 wt. % to 2 wt. % water and a ketone stream selected from the group consisting of an acetone stream, a MEK stream, and a mixed acetone/MEK stream; and
   said cleavage reaction conditions comprise feeding the first cleavage reaction feed to a first cleavage reactor and subjecting the first cleavage reaction feed to first cleavage reaction conditions effective to produce a first cleavage reaction product comprising a first cleavage reaction mixture, and feeding the first cleavage reaction product to a second cleavage reactor to produce a second cleavage reaction mixture and subjecting the second cleavage reaction mixture to second cleavage reaction conditions effective to produce a second cleavage reaction product.

3. The process of claim 2 wherein the second cleavage reaction conditions comprise a second cleavage reaction temperature effective convert DMBA to α-methyl styrene and to convert EMBA to one or more compound selected from the group consisting of α-ethyl styrene (AES), 2-phenyl-2-butene (2P2B), and combinations thereof.

4. The process of claim 1 wherein said first cleavage reaction conditions comprise feeding to the first cleavage reaction mixture an acid catalyst effective to catalyze the cleavage of hydroperoxides selected from the group consisting of s-butylbenzene hydroperoxide, cumene hydroperoxide, and combinations thereof.

5. The process of claim 2 wherein said first cleavage reaction conditions comprise feeding to the first cleavage reaction mixture an acid catalyst effective to catalyze the cleavage of hydroperoxides selected from the group consisting of s-butylbenzene hydroperoxide, cumene hydroperoxide, and combinations thereof.

6. The process of claim 3 wherein said first cleavage reaction conditions comprise feeding to the first cleavage reaction mixture an acid catalyst effective to catalyze the cleavage of hydroperoxides selected from the group consisting of s-butylbenzene hydroperoxide, cumene hydroperoxide, and combinations thereof.

7. The process of claim 4 wherein the acid catalyst is selected from the group consisting of sulfuric acid, sulfuric acid anhydride, perchioric acid, and phosphoric acid.

8. The process of claim 5 wherein the acid catalyst is selected from the group consisting of sulfuric acid, sulfuric acid anhydride, perchloric acid, and phosphoric acid.

9. The process of claim 6 wherein the acid catalyst is selected from the group consisting of sulfuric acid, sulfuric acid anhydride, perchloric acid, and phosphoric acid.

10. The process of claim 4 wherein the acid catalyst comprises sulfuric acid.

11. The process of claim 5 wherein the acid catalyst comprises sulfuric acid.

12. The process of claim 6 wherein the acid catalyst comprises sulfuric acid.

13. The process of claim 6 wherein the second cleavage reactor is selected from the group consisting of plug-flow reactors, plug-flow reactors with recycle, and continuous stirred tank reactors.

14. The process of claim 12 wherein the second cleavage reactor is selected from the group consisting of plug-flow reactors, plug-flow reactors with recycle, and continuous stirred tank reactors.

15. The process of claim 1 wherein the first cleavage reaction conditions comprise
   a first cleavage reaction temperature of from about 45° C. to about 70° C.;
   a first cleavage reaction pressure sufficiently high to maintain the first cleavage reaction mixture in the liquid phase; and,
   a first cleavage reaction residence time effective to cleave about 95% or more of s-butylbenzene hydroperoxide in the first cleavage reaction mixture to phenol and MEK and to cleave about 95% or more of cumene hydroperoxide in the first cleavage reaction mixture to phenol and acetone.

16. The process of claim 2 wherein the first cleavage reaction conditions comprise
   a first cleavage reaction temperature of from about 45° C. to about 70° C.;

a first cleavage reaction pressure sufficiently high to maintain the first cleavage reaction mixture in the liquid phase; and, a first cleavage reaction residence time effective to cleave about 95% or more of s-butylbenzene hydroperoxide in the first cleavage reaction mixture to phenol and MEK and to cleave about 95% or more of cuinene hydroperoxide in the first cleavage reaction mixture to phenol and acetone.

17. The process of claim 3 wherein the first cleavage reaction conditions comprise a first cleavage reaction temperature of from about 45° C. to about 70° C.;

a first cleavage reaction pressure sufficiently high to maintain the first cleavage reaction mixture in the liquid phase; and, a first cleavage reaction residence time effective to cleave about 95% or more of s-butylbenzene hydroperoxide in the first cleavage reaction mixture to phenol and MEK and to cleave about 95% or more of cumene hydroperoxide in the first cleavage reaction mixture to phenol and acetone.

18. The process of claim 4 wherein the first cleavage reaction conditions comprise a first cleavage reaction temperature of from about 45° C. to about 70° C.;

a first cleavage reaction pressure sufficiently high to maintain the first cleavage reaction mixture in the liquid phase; and, a first cleavage reaction residence time effective to cleave about 95% or more of s-butylbenzene hydroperoxide in the first cleavage reaction mixture to phenol and MEK and to cleave about 95% or more of cumene hydroperoxide in the first cleavage reaction mixture to phenol and acetone.

19. The process of claim 6 wherein the first cleavage reaction conditions comprise a first cleavage reaction temperature of from about 45° C. to about 70° C.;

a first cleavage reaction pressure sufficiently high to maintain the first cleavage reaction mixture in the liquid phase; and, a first cleavage reaction residence time effective to cleave about 95% or more of s-butylbenzene hydroperoxide in the first cleavage reaction mixture to phenol and MEK and to cleave about 95% or more of cumene hydroperoxide in the first cleavage reaction mixture to phenol and acetone.

20. The process of claim 12 wherein the first cleavage reaction conditions comprise a first cleavage reaction temperature of from about 45° C. to about 70° C.;

a first cleavage reaction pressure sufficiently high to maintain the first cleavage reaction mixture in the liquid phase; and, a first cleavage reaction residence time effective to cleave about 95% or more of s-butylbenzene hydroperoxide in the first cleavage reaction mixture to phenol and MEK and to cleave about 95% or more of cumene hydroperoxide in the first cleavage reaction mixture to phenol and acetone.

21. The process of claim 19 wherein the first cleavage reaction temperature is from about 45° C. to about 60° C.

22. The process of claim 20 wherein the first cleavage reaction temperature is from about 45° C. to about 60° C.

23. he process of claim 19 wherein the first cleavage reaction temperature is from about 45° C. to about 55° C.

24. The process of claim 20 wherein the first cleavage reaction temperature is from about 45° C. to about 55° C.

25. The process of claim 23 wherein the first cleavage reaction conditions comprise a first cleavage reaction pressure of about 0.5 atmosphere or more.

26. The process of claim 24 wherein the first cleavage reaction conditions comprise a first cleavage reaction pressure of about 0.5 atmosphere or more.

27. The process of claim 1 wherein the first cleavage reaction conditions comprise recirculating a recycle flow of the first cleavage reaction mixture through the first cleavage reactor.

28. The process of claim 2 wherein the first cleavage reaction conditions comprise recirculating a recycle flow of the first cleavage reaction mixture through the first cleavage reactor.

29. The process of claim 3 wherein the first cleavage reaction conditions comprise recirculating a recycle flow of the first cleavage reaction mixture through the first cleavage reactor.

30. The process of claim 4 wherein the first cleavage reaction conditions comprise recirculating a recycle flow of the first cleavage reaction mixture through the first. cleavage reactor.

31. The process of claim 6 wherein the first cleavage reaction conditions comprise recirculating a recycle flow of the first cleavage reaction mixture through the first cleavage reactor.

32. The process of claim 12 wherein the first cleavage reaction conditions comprise recirculating a recycle flow of the first cleavage reaction mixture through the first cleavage reactor.

33. The process of claim 20 wherein the first cleavage reaction conditions comprise recirculating a recycle flow of the first cleavage reaction mixture through the first cleavage reactor.

34. The process of claim 27 further comprising withdrawing the first cleavage reaction product from the first cleavage reactor at a first cleavage reaction product withdrawal point upstream of the first cleavage reactor feed.

35. The process of claim 33 further comprising withdrawing the first cleavage reaction product from the first cleavage reactor at a first cleavage reaction product withdrawal point upstream of the first cleavage reactor feed.

36. The process of claim 27 wherein the recycle flow is greater than the first cleavage reactor feed flow.

37. The process of claim 29 wherein the recycle flow is greater than the first cleavage reactor feed flow.

38. The process of claim 31 wherein the recycle flow is greater than the first cleavage reactor feed flow.

39. The process of claim 33 wherein the recycle flow is greater than the first cleavage reactor feed flow.

40. The process of claim 35 wherein the recycle flow is greater than the first cleavage reactor feed flow.

41. The process of claim 27 wherein a ratio of the recycle flow to the first cleavage reactor feed flow is from about 10:1 to about 100:1 on a weight basis.

42. The process of claim 31 wherein a ratio of the recycle flow to the first cleavage reactor feed flow is from about 10:1 to about 100:1 on a weight basis.

43. The process of claim 27 wherein a ratio of the recycle flow to the first cleavage reactor feed flow is from about 20:1 to 40:1 on a weight basis.

44. The process of claim 31 wherein a ratio of the recycle flow to the first cleavage reactor feed flow is from about 20:1 to 40:1 on a weight basis.

45. The process of claim 39 wherein the first cleavage reaction conditions comprise a first cleavage reaction residence time effective to cleave from about 95% to about 98% of s-butylbenzene hydroperoxide in the first cleavage reaction mixture to phenol and MEK.

46. The process of claim 37 wherein the first cleavage reaction residence time is from about 1 minute to about 10 minutes.

47. The process of claim 39 wherein the first cleavage reaction residence time is from about 1 minute to about 10 minutes.

48. The process of claim 2 wherein the second cleavage reactor comprises a once through plug flow reactor.

49. The process of claim 31 further comprising adding the acid catalyst to a first cleavage reaction mixture side stream at one or more acid addition points.

50. The process of claim 39 further comprising adding the acid catalyst to a first cleavage reaction mixture side stream at one or more acid addition points.

51. The process of claim 3 wherein the second cleavage reaction conditions comprise a second cleavage reaction temperature and a second cleavage reaction residence time effective to cleave 95 wt. % or more of the hydroperoxides remaining in the second cleavage reaction mixture.

52. The process of claim 40 wherein the second cleavage reaction conditions comprise a second cleavage reaction temperature and a second cleavage reaction residence time effective to cleave 95 wt. % or more of the hydroperoxides remaining in the second cleavage reaction mixture.

53. The process of claim 34 further comprising withdrawing the first cleavage reaction mixture side stream between the first cleavage reaction product withdrawal point and the first cleavage reactor feed point.

54. The process of claim 35 further comprising withdrawing the first cleavage reaction mixture side stream between the first cleavage reaction product withdrawal point and the first cleavage reactor feed point.

55. The process of claim 52 wherein the second cleavage reaction conditions are effective to convert 70 wt. % or more of DMBA in the first cleavage reaction product to AMS.

56. The process of claim 55 wherein the second cleavage reaction conditions are effective to convert 70 wt. % or more of EMBA in the first cleavage reaction product to ABS, 2P2B, and combinations thereof.

57. The process of claim 52 wherein the second cleavage reaction conditions are effective to convert 75 wt. % or more of DMBA in the first cleavage reaction product to ANS.

58. The process of claim 55 wherein the second cleavage reaction conditions are effective to convert 75 wt. % or more of EMBA in the first cleavage reaction product to AES, 2P2B, and combinations thereof.

59. The process of claim 52 wherein the second cleavage reaction conditions are effective to convert 85 wt. % or more of DMBA in the first cleavage reaction product to AMS.

60. The process of claim 55 wherein the second cleavage reaction conditions are effective to convert 85 wt. % or more of EMBA in the first cleavage reaction product to ABS, 2P2B, and combinations thereof.

61. A process for cleaving a mixture of s-butylbenzene hydroperoxide and cumene hydroperoxide, the process comprising:
feeding to a first cleavage reactor at a first cleavage reaction feed flow a cleavage reaction feed comprising from about 0.5 wt. % to 2 wt. % water, a ketone stream selected from the group consisting of an acetone stream, a MEK stream, and a mixed acetone/MEK stream, s-butylbenzene hydroperoxide and cumene hydroperoxide, and an acid catalyst effective to catalyze the cleavage of s-butylbenzene hydroperoxide and cumene hydroperoxide, producing a first cleavage reaction mixture;
exposing said first cleavage reaction mixture to first cleavage reaction conditions effective to cleave s-butylbenzene hydroperoxide to phenol and MEK and to cleave cuinene hydroperoxide to phenol and acetone, wherein said first cleavage reaction conditions comprise:
a first cleavage reaction temperature of less than 75° C. which is sufficiently high to cleave a majority of the hydroperoxides but sufficiently low to produce a first quantity of non-recoverable byproducts from components selected from the group consisting of dimethylbenzyl alcohol (DMBA), ethyl methyl benzyl carbinol (EMBA), and combinations thereof, the first quantity of said non-recoverable byproducts being less than a second quantity of said non-recoverable byproducts produced by the same process at a cleavage reaction temperature of 75° C. or higher;
a first cleavage reaction pressure sufficiently high to maintain the first cleavage reaction mixture in the liquid phase;
recirculating a recycle flow of the first cleavage reaction mixture through the first cleavage reactor, said recycle flow being greater than the first cleavage reactor feed flow; and
feeding the first cleavage reaction product to a second cleavage reactor to produce a second cleavage reaction mixture;
subjecting the second cleavage reaction mixture to second cleavage reaction conditions comprising a second cleavage reaction temperature effective to cleave 95 wt. % or more of the hydroperoxides remaining in the second cleavage reaction mixture, to convert a majority of DMBA in the second cleavage reaction mixture to α-methyl styrene, and to convert a majority of EMBA in the second cleavage reaction mixture to one or more compound selected from the group consisting of α-ethyl styrene (AES), 2-phenyl-2-butene (2P2B), and combinations thereof, producing a second cleavage reaction product; and,
subjecting the second cleavage reaction product to final conditions effective to produce a final cleavage reaction product comprising phenol and one or more component selected from the group consisting of methyl ethyl ketone (MEK), acetone, and combinations thereof.

62. The process of claim 61 wherein a ratio of the recycle flow to the first cleavage reactor feed flow is from about 10:1 to about 100:1 on a weight basis.

63. The process of claim 61 wherein a ratio of the recycle flow to the first cleavage reactor feed flow is from about 20:1 to 40:1 on a weight basis.

64. The process of claim 61 wherein the first cleavage reaction conditions comprise a first cleavage reaction residence time effective to cleave about 95% or more of s-butylbenzene hydroperoxide in the first cleavage reaction mixture to phenol and MEK.

65. The process of claim 63 wherein the first cleavage reaction conditions comprise a first cleavage reaction residence time effective to cleave about 95% or more of s-butylbenzene hydroperoxide in the first cleavage reaction mixture to phenol and MEK.

66. The process of claim 61 wherein the first cleavage reaction conditions comprise a first cleavage reaction residence time effective to cleave from about 95% to about 98% of s-butylbenzene hydroperoxide in the first cleavage reaction mixture to phenol and MEK.

67. The process of claim 61 wherein the first cleavage reaction conditions comprise a first cleavage reaction residence time effective to cleave about 95% or more of cumene hydroperoxide in the first cleavage reaction mixture to phenol and acetone.

68. The process of claim 64 wherein the first cleavage reaction conditions comprise a first cleavage reaction residence time effective to cleave about 95% or more of cumene hydroperoxide in the first cleavage reaction mixture to phenol and acetone.

69. The process of claim 65 wherein the first cleavage reaction conditions comprise a first cleavage reaction residence time effective to cleave about 95% or more of cumene hydroperoxide in the first cleavage reaction mixture to phenol and acetone.

70. The process of claim 68 wherein the first cleavage reaction residence time is from about 1 minute to about 10 minutes.

71. The process of claim 69 wherein the first cleavage reaction residence time is from about 1 minute to about 10 minutes.

72. The process of claim 68 wherein the acid catalyst is selected from the group consisting of sulfuric acid, sulfuric acid anhydride, perchloric acid, and phosphoric acid.

73. The process of claim 68 wherein the acid catalyst comprises sulfuric acid.

74. The process of claim 68 further comprising adding the acid catalyst to a first cleavage reaction mixture side stream at one or more acid addition points.

75. The process of claim 72 further comprising adding the acid catalyst to a first cleavage reaction mixture side stream at one or more acid addition points.

76. The process of claim 73 further comprising adding the acid catalyst to a first cleavage reaction mixture side stream at one or more acid addition points.

77. The process of claim 61 further comprising withdrawing the first cleavage reaction mixture side stream between the first cleavage reaction product withdrawal point and the first cleavage reactor feed point.

78. The process of claim 74 further comprising withdrawing the first cleavage reaction product from the first cleavage reactor at a first cleavage reaction product withdrawal point upstream of the first cleavage reactor feed.

79. The process of claim 61 wherein the second cleavage reaction conditions are effective to convert 70 wt. % or more of DMBA in the first cleavage reaction product to AMS.

80. The process of claim 61 wherein the second cleavage reaction conditions are effective to convert 70 wt. % or more of EMBA in the first cleavage reaction product to AES, 2P2B, and combinations thereof.

81. The process of claim 61 wherein the second cleavage reaction conditions are effective to convert 75 wt. % or more of DMBA in the first cleavage reaction product to AMS.

82. The process of claim 61 wherein the second cleavage reaction conditions are effective to convert 75 wt. % or more of EMBA in the first cleavage reaction product to AES, 2P2B, and combinations thereof.

83. The process of claim 61 wherein the second cleavage reaction conditions are effective to convert 85 wt. % or more of DMBA in the first cleavage reaction product to AMS.

84. The process of claim 61 wherein the second cleavage reaction conditions are effective to convert 85 wt. % or more of EMBA in the first cleavage reaction product to AES, 2P2B, and combinations thereof.

85. A process for cleaving one or more hydroperoxides selected from the group consisting of s-butylbenzene hydroperoxide, cumene hydroperoxide, and combinations thereof, the process comprising:

feeding a cleavage reaction feed comprising from about 0.5 wt. % to 2 wt. % water, a ketone stream selected from the group consisting of an acetone stream, a MEK stream, and a mixed acetone/MEK stream, and an acid catalyst to a first cleavage reactor at a first cleavage reaction feed flow, producing a first cleavage reaction mixture, said acid catalyst being effective to catalyze the cleavage of hydroperoxides selected from the group consisting of s-butylbenzene hydroperoxide, cuinene hydroperoxide, and combinations thereof;

exposing said first cleavage reaction mixture to first cleavage reaction conditions effective to produce a first cleavage reaction product comprising the one or more hydroperoxides, said first cleavage reaction conditions comprising a first cleavage reaction temperature of less than 75° C. and a first cleavage reaction pressure sufficiently high to maintain the first cleavage reaction mixture in the liquid phase, said first cleavage reaction conditions further comprising recirculating a recycle flow of the first cleavage reaction mixture through the first cleavage reactor, wherein the ratio of said recycle flow to said first cleavage reactor feed flow is from about 10:1 to about 100:1 on a weight basis, said first cleavage reaction conditions being effective to cleave about 95% or more of s-butylbenzene hydroperoxide in the first cleavage reaction mixture to phenol and MEK, to cleave about 95% or more of cumene hydroperoxide in the first cleavage reaction mixture to phenol and acetone, and to produce a first quantity of non-recoverable byproducts from components selected from the group consisting of dimethylbenzyl alcohol (DMBA), ethyl methyl benzyl carbinol (EMBA), and combinations thereof, the first quantity of said non-recoverable byproducts being less than a second quantity of said non-recoverable byproducts produced by the same process at a cleavage reaction temperature of 75° C. or higher; and feeding the first cleavage reaction product to a second cleavage reactor to produce a second cleavage reaction mixture;

subjecting the second cleavage reaction mixture to second cleavage reaction conditions comprising a second cleavage reaction temperature effective to cleave 95 wt. % or more of the hydroperoxides remaining in the second cleavage reaction mixture, to convert 70 wt. % or more of DMBA in the second cleavage reaction mixture to α-methyl styrene, and to convert 70 wt. % or more of EMBA in the second cleavage reaction mixture to one or more compound selected from the group consisting of α-ethyl styrene (AES), 2-phenyl-2-butene (2P2B), and combinations thereof, producing a second cleavage reaction product; and, subjecting the second cleavage reaction product to final conditions effective to produce a final cleavage reaction product comprising phenol and one or more component selected from the group consisting of methyl ethyl ketone (MEK), acetone, and combinations thereof.

86. The process of claim 85 wherein said second cleavage reaction conditions comprise a second cleavage reaction temperature effective to cleave 95 wt. % or more of the hydroperoxides renaming in the second cleavage reaction mixture, to convert 75 wt. % or more of DMBA in the second cleavage reaction mixture to α-methyl styrene, and to convert 75 wt. % or more of EMBA in the second cleavage reaction mixture to one or more compound selected from the group consisting of α-ethyl styrene (AES), 2-phenyl-2-butene (2P2B), and combinations thereof.

87. The process of claim 85 wherein said second cleavage reaction conditions comprise a second cleavage reaction temperature effective to cleave 95 wt. % or more of the hydroperoxides remaining in the second cleavage reaction mixture, to convert 85 wt. % or more of DMBA in the second cleavage reaction mixture to α-methyl styrene, and to convert 85 wt. % or more of EMBA in the second cleavage reaction mixture to one or more compound selected from the group consisting of α-methyl styrene (ABS), 2-phenyl-2-butene (2P2B), and combinations thereof, 88. The process of claim 85 wherein the first cleavage reactor is a pipeline loop reactor comprising one or more heat exchangers effective to maintain a first cleavage reaction mixture at a first cleavage reaction temperature.

89. The process of claim 86 wherein the first cleavage reactor is a pipeline loop reactor comprising one or more heat exchangers effective to maintain a first cleavage reaction mixture at a first cleavage reaction temperature.

90. The process of claim 87 wherein the first cleavage reactor is a pipeline loop reactor comprising one or more heat exchangers effective to maintain a first cleavage reaction mixture at a first cleavage reaction temperature.

91. The process of claim 85 wherein the first cleavage reaction conditions comprise a first cleavage reaction temperature of from about 45° C. to about 70° C.

92. The process of claim 86 wherein the first cleavage reaction conditions comprise a first cleavage reaction temperature of from about 45° C. to about 70° C.

93. The process of claim 87 wherein the first cleavage reaction conditions comprise a first cleavage reaction temperature of from about 45° C. to about 70° C.

94. The process of claim 88 wherein the first cleavage reaction conditions comprise a first cleavage reaction temperature of from about 45° C. to about 70° C.

95. The process of claim 89 wherein the first cleavage reaction conditions comprise a first cleavage reaction temperature of from about 45° C. to about 70° C.

96. The process of claim 90 wherein the first cleavage reaction conditions comprise a first cleavage reaction temperature of from about 45° C. to about 70° C.

97. The process of claim 85 wherein the first cleavage reaction conditions comprise a first cleavage reaction temperature of from about 45° C. to about 60° C.

98. The process of claim 86 wherein the first cleavage reaction conditions comprise a first cleavage reaction temperature of from about 45° C. to about 60° C.

99. The process of claim 87 wherein the first cleavage reaction conditions comprise a first cleavage reaction temperature of from about 45° C. to about 60° C.

100. The process of claim 88 wherein the first cleavage reaction conditions comprise a first cleavage reaction temperature of from about 45° C. to about 60° C.

101. The process of claim 89 wherein the first cleavage reaction conditions comprise a first cleavage reaction temperature of from about 45° C. to about 60° C.

102. The process of claim 90 wherein the first cleavage reaction conditions comprise a first cleavage reaction temperature of from about 45° C. to about 60° C.

103. The process of claim 87 wherein the first cleavage reaction conditions comprise a first cleavage reaction temperature of from about 45° C. to about 55° C.

104. The process of claim 88 wherein the first cleavage reaction conditions comprise a first cleavage reaction temperature of from about 45° C. to about 55° C.

105. The process of claim 89 wherein the first cleavage reaction conditions comprise a first cleavage reaction temperature of from about 45° C. to about 55° C.

106. The process of claim 90 wherein the first cleavage reaction conditions comprise a first cleavage reaction temperature of from about 45° C. to about 55° C.

107. The process of claim 106 wherein the first cleavage reaction conditions comprise a first cleavage reaction pressure of about 0.5 or less.

108. The process of claim 85 further comprising withdrawing the first cleavage reaction product from the first cleavage reactor at a first cleavage reaction product withdrawal point upstream of the first cleavage reactor feed.

109. The process of claim 107 further comprising withdrawing the first cleavage reaction product from the first cleavage reactor at a first cleavage reaction product withdrawal point upstream of the first cleavage reactor feed.

110. The process of claim 85 wherein a ratio of the recycle flow to the first cleavage reactor feed flow is from about 20:1 to 40:1 on a weight basis.

111. The process of claim 107 wherein a ratio of the recycle flow to the first cleavage reactor feed flow is from about 20:1 to 40:1 on a weight basis.

112. The process of claim 107 wherein the first cleavage reaction residence time is from about 1 minute to about 10 minutes.

113. The process of claim 107 wherein the acid catalyst is selected from the group consisting of sulfuric acid, sulfuric acid anhydride, perchloric acid, and phosphoric acid.

114. The process of claim 85 wherein the acid catalyst comprises sulfuric acid.

115. The process of claim 112 wherein the acid catalyst comprises sulfuric acid.

116. The process of claim 85 further comprising adding the acid catalyst to a first cleavage reaction mixture side stream at one or more acid addition points.

117. The process of claim 115 further comprising adding the acid catalyst to a first cleavage reaction mixture side stream at one or more acid addition points.

118. The process of claim 94 further comprising withdrawing the first cleavage reaction mixture side stream between the first cleavage reaction product withdrawal point and the first cleavage reactor feed point.

119. The process of claim 95 further comprising withdrawing the first cleavage reaction mixture side stream between the first cleavage reaction product withdrawal point and the first cleavage reactor feed point.

120. The process of claim 118 wherein the amount of acid catalyst fed to the first cleavage reactor is from about 0.005% to about 0.1% by weight based on the first cleavage reactor feed flow.

121. The process of claim 119 wherein the amount of acid catalyst fed to the first cleavage reactor is from about 0.005% to about 0.1% by weight based on the first cleavage reactor feed flow.

122. The process of claim 85 wherein the second cleavage reactor comprises a once through plug flow reactor.

123. The process of claim 120 wherein the second cleavage reactor comprises a once through plug flow reactor.

124. The process of claim 121 wherein the second cleavage reactor comprises a once through plug flow reactor.

125. The process of claim 85 wherein the second cleavage reaction conditions comprise a second cleavage reaction residence time of from about 5 seconds to about 1 minute.

126. The process of claim 85 wherein the second cleavage reaction temperature is from about 60° C. to about 130° C.

127. The process of claim 124 wherein the second cleavage reaction temperature is from about 60° C. to about 130° C.

128. The process of claim 125 wherein the second cleavage reaction temperature is from about 60° C. to about 130° C.

129. The process of claim 105 wherein the second cleavage reaction temperature is from about 70° C. to about 120° C.

130. The process of claim 126 wherein the second cleavage reaction pressure is about 30 psig or more.

131. The process of claim 85 further comprising taking multiple exotherm measurements to verify the rate of the cleavage reaction.

132. The process of claim 130 further comprising taking multiple exotherm measurements to verify the rate of the cleavage reaction.

133. The process of claim 131 further comprising controlling the amount of acid catalyst added to the first cleavage reaction mixture based on the multiple exotherm measurements.

134. The process of claim 132 further comprising controlling the amount of acid catalyst added to the first cleavage reaction mixture based on the multiple exotherm measurements.

135. The process of claim 133 wherein taking the multiple exotherm measurements comprises
   taking a first reaction mixture side stream exotherm measurement;
   taking a first cleavage reactor (FCR) exotherm measurement; and,
   taking a second cleavage reactor (SCR) exotherm measurement.

136. The process of claim 134 wherein taking the multiple exotherm measurements comprises
   taking a first reaction mixture side stream exotherm measurement;
   taking a first cleavage reactor (FCR) exotherm measurement; and,
   taking a second cleavage reactor (SCR) exotherm measurement.

137. A process for cleaving one or more hydroperoxides selected from the group consisting of s-butylbenzene hydroperoxide, cumene hydroperoxide, and combinations thereof, the process comprising:
   feeding a cleavage reaction feed to a cleavage reactor to produce a cleavage reaction mixture comprising the one or more hydroperoxides; and
   subjecting the cleavage reaction mixture to cleavage reaction conditions effective to produce a cleavage reaction product comprising phenol and one or more components selected from the group consisting of methyl ethyl ketone (MEK), acetone, and combinations thereof;
   wherein the cleavage reaction conditions comprise a cleavage reaction temperature of less than 75° C. which is sufficiently high to cleave a majority of the one or more hydroperoxides but sufficiently low to produce a first quantity of non-recoverable byproducts from components selected from the group consisting of dimethylbenzyl alcohol (DMBA), ethyl methyl benzyl carbinol (EMBA), and combinations thereof, the first quantity of said non-recoverable byproducts being less than a second quantity of said non-recoverable byproducts produced by the same process at a cleavage reaction temperature of 75° C. or higher; and
   feeding the cleavage reaction product to a second cleavage reactor comprising a once through plug flow reactor.

138. A process for cleaving one or more hydroperoxides selected from the group consisting of s-butylbenzene hydroperoxide, cumene hydroperoxide, and combinations thereof, the process comprising:
   feeding a cleavage reaction feed comprising the one or more hydroperoxides and from about 0.5 wt. % to 2 wt. % water and a ketone stream selected from the group consisting of an acetone stream, a MEK stream, and a mixed acetone/MEK stream to a first cleavage reactor to produce a cleavage reaction mixture;
   subjecting the cleavage reaction mixture to cleavage reaction conditions effective to produce a first cleavage reaction product comprising phenol and one or more components selected from the group consisting of methyl ethyl ketone (MEK), acetone, and combinations thereof;
   wherein the cleavage reaction conditions comprise a cleavage reaction temperature of less than 75° C. which is sufficiently high to cleave a majority of the one or more hydroperoxides but sufficiently low to produce a first quantity of non-recoverable byproducts from components selected from the group consisting of dimethylbenzyl alcohol (DMBA), ethyl methyl benzyl carbinol (EMBA), and combinations thereof, the first quantity of said non-recoverable byproducts being less than a second quantity of said non-recoverable byproducts produced by the same process at a cleavage reaction temperature of 75° C. or higher; and
   feeding the first cleavage reaction product to a second cleavage reactor operating at second cleavage reaction conditions comprising a second cleavage reaction temperature and a second cleavage residence time effective to convert DMBA to α-methyl styrene and to convert EMBA to one or more compound selected from the group consisting of α-ethyl styrene (AES), 2-phenyl-2-butene (2P2B), and combinations thereof and to cleave 95 wt. % or more of the hydroperoxides remaining in the second cleavage reaction mixture.

139. The process of claim 138 wherein the second cleavage reaction conditions are effective to convert 70 wt. % or more of DMBA in the first cleavage reaction product to AMS.

140. The process of claim 138 wherein the second cleavage reaction conditions are effective to convert 70 wt. % or more of EMBA in the first cleavage reaction product to AES, 2P2B, and combinations thereof.

141. The process of claim 52 wherein the second cleavage reaction conditions are effective to convert 85 wt. % or more of DMBA in the first cleavage reaction product to AMS.

142. The process of claim 55 wherein the second cleavage reaction conditions are effective to convert 85 wt. % or more of EMBA in the first cleavage reaction product to AES, 2P2B, and combinations thereof.

* * * * *